United States Patent
Shiao (10) Patent No.: US 9,987,041 B2
(45) Date of Patent: Jun. 5, 2018

(54) DISPOSABLE NEEDLE HAIR TRANSPLANTER

(71) Applicant: FOLLICULAR TECHNOLOGIES, LLC, Los Angeles, CA (US)

(72) Inventor: Tseng-Kuo Shiao, Taipei (TW)

(*) Notice: Subject to any disclaimer, the term of this patent is extended or adjusted under 35 U.S.C. 154(b) by 307 days.

(21) Appl. No.: 14/531,737

(22) Filed: Nov. 3, 2014

(65) Prior Publication Data
US 2016/0120574 A1    May 5, 2016

(51) Int. Cl.
- *A61B 17/34* (2006.01)
- *A61F 2/10* (2006.01)
- *A61B 17/00* (2006.01)

(52) U.S. Cl.
CPC ........... *A61B 17/3468* (2013.01); *A61F 2/10* (2013.01); *A61B 17/3494* (2013.01); *A61B 2017/0023* (2013.01); *A61B 2017/00752* (2013.01)

(58) Field of Classification Search
CPC .......... A61B 17/32093; A61B 17/3403; A61B 2017/3405; A61B 2017/3407; A61B 17/3468; A61B 2017/347; A61B 17/3417; A61B 17/3496; A61B 2017/00752; A61B 17/32053; A61B 17/3494; A61B 2017/0023; A61B 2017/348; A61B 2017/3492; A61F 2/10
USPC ................................ 606/133, 172, 184, 185
See application file for complete search history.

(56) References Cited

U.S. PATENT DOCUMENTS

| | | | | |
|---|---|---|---|---|
| 3,596,292 A * | 8/1971 | Erb | ........................... | A61F 2/10 132/200 |
| 5,417,683 A * | 5/1995 | Shiao | ................. | A61B 17/3468 604/173 |
| 5,538,010 A * | 7/1996 | Darr | .................... | A61B 10/0275 600/567 |
| 5,817,120 A * | 10/1998 | Rassman | ............ | A61B 17/3468 606/185 |
| 7,261,721 B2 * | 8/2007 | Feller | ................ | A61B 17/32053 128/898 |
| 7,452,367 B2 * | 11/2008 | Rassman | ............ | A61B 17/3468 600/566 |
| 7,780,635 B2 * | 8/2010 | Pruitt | ................ | A61M 5/31586 604/187 |

(Continued)

OTHER PUBLICATIONS http://www.dictionary.com/browse/threaded retrieved Sep. 15, 2016.*

*Primary Examiner* — Ryan J Severson
(74) *Attorney, Agent, or Firm* — Eric B. Alspaugh (57) ABSTRACT

A disposable needle hair transplanter includes: a plunger structure having an outer barrel defining a passage, a plunger assembly having at least one push needle movable within the passage of the outer barrel, and a hair transplantation depth controller drivingly connected with the plunger assembly via a link; a needle having a needle seat connected with the outer barrel and at least one needle tube in which a hair follicle is loadable, the hair transplantation depth controller serving to restrict the depth by which the needle tube is thrust into the scalp; and a hair follicle depth controller having a cylindrical structure fitted around the needle seat and a shaft tube connected with the cylindrical structure and coaxially disposed around the needle tube. The hair transplantation depth controller is disposed around the shaft tube and movable along the shaft tube toward or away from the scalp.

11 Claims, 7 Drawing Sheets

(56) References Cited

U.S. PATENT DOCUMENTS

| | | | | |
|---|---|---|---|---|
| 7,785,339 B2* | 8/2010 | Cohen | A61B 17/32053 | 606/131 |
| 8,062,322 B2* | 11/2011 | Rassman | A61B 17/3468 | 600/566 |
| 8,206,335 B2* | 6/2012 | Pruitt | A61M 5/31586 | 222/309 |
| 8,801,743 B2* | 8/2014 | Giotis | A61B 17/32053 | 606/187 |
| 9,005,218 B2* | 4/2015 | Harris | A61B 17/32053 | 606/133 |
| 9,198,686 B2* | 12/2015 | Motai | A61B 10/0233 | |
| 9,480,496 B2* | 11/2016 | Cole | A61B 17/32053 | |
| 9,492,196 B2* | 11/2016 | Keren | A61B 17/3468 | |
| 2003/0036770 A1* | 2/2003 | Markman | A61B 17/3468 | 606/187 |
| 2004/0116942 A1* | 6/2004 | Feller | A61B 17/32053 | 606/133 |
| 2005/0096687 A1* | 5/2005 | Rassman | A61B 17/3468 | 606/187 |
| 2005/0187573 A1* | 8/2005 | Rassman | A61B 17/3468 | 606/187 |
| 2007/0038236 A1* | 2/2007 | Cohen | A61B 17/32053 | 606/187 |
| 2007/0156164 A1* | 7/2007 | Cole | A61B 17/32053 | 606/187 |
| 2007/0233038 A1* | 10/2007 | Pruitt | A61M 5/31586 | 604/522 |
| 2010/0114118 A1* | 5/2010 | Harris | A61B 17/32053 | 606/133 |
| 2010/0125287 A1* | 5/2010 | Cole | A61B 17/32053 | 606/133 |
| 2010/0280488 A1* | 11/2010 | Pruitt | A61M 5/31586 | 604/506 |
| 2011/0319921 A1* | 12/2011 | Giotis | A61B 17/32053 | 606/187 |
| 2012/0245612 A1* | 9/2012 | Keren | A61B 17/3468 | 606/187 |
| 2012/0283656 A1* | 11/2012 | Pruitt | A61M 5/31586 | 604/211 |
| 2012/0289985 A1* | 11/2012 | Motai | A61B 10/0233 | 606/185 |
| 2013/0226212 A9* | 8/2013 | Giotis | A61B 17/32053 | 606/187 |
| 2014/0188150 A1* | 7/2014 | Oc | A61F 2/10 | 606/187 |
| 2016/0120574 A1* | 5/2016 | Shiao | A61B 17/3468 | 606/187 |
| 2016/0166272 A1* | 6/2016 | Shiao | A61B 17/32053 | 606/133 |
| 2016/0213400 A1* | 7/2016 | Oc | A61B 17/3468 | |

* cited by examiner

DISPOSABLE NEEDLE HAIR TRANSPLANTER

BACKGROUND OF THE INVENTION

1. Field of the Invention

The present invention relates generally to a disposable needle hair transplanter.

2. Description of the Related Art

Usually, baldness happens to a range covering the forehead, the top and upper side of the occiput. Baldness of these parts is a critical defect to males. Some bald-headed males go through hair transplantation program to solve the baldness problem. In recent ten years, the hair transplantation technique has made enormous progress. Currently, micro hair transplantation is globally employed to treat baldness. That is, only one single hair follicle is transplanted in each grafting. The hair follicle is extracted from the scalp of the back of a patient's head by means of microscope technique. Each hair follicle contains 1-4 hairs. The diameter of the hair follicle ranges from 1 mm to 2 mm and the length of the hair follicle ranges from 5 mm to 6 mm. The hair follicle is quite slender and fine.

With respect to the existent hair transplantation technique, the hair follicle is generally grafted with a small pair of pincers. First, a No. 18 or No. 19 needle tube is thrust into the scalp to form an orifice. Then the small pair of pincers is used to clamp the root section of the hair follicle to plug the hair follicle into the orifice. The orifice formed by the thrust of the needle tube is so small that it is uneasy to plug the hair follicle into the orifice. It often takes place that the hair follicle is damaged and dead after several times of failure in the plugging process. Also, in the case that the hair follicle is too tightly clamped by the pincers, the hair follicle is very likely to die. In the current micro hair transplantation process, an operator often comes across the above problems.

In order to solve the above problems, various hair transplanters have been developed. The operation of the hair transplanter only necessitates two steps. First, the needle tube is thrust into the scalp to fissure the scalp. Then, the hair follicle is transplanted. Only one hair follicle can be transplanted with one needle tube at one time. To a patient who needs dense hair transplantation, it costs pretty much time to complete the hair transplantation process.

SUMMARY OF THE INVENTION

It is therefore a primary object of the present invention to provide a hair transplanter, which can transplant at least one hair follicle at one time to shorten the hair transplantation time.

It is a further object of the present invention to provide a hair transplanter, which can fissure the scalp and transplant the hair follicle at the same time.

It is still a further object of the present invention to provide a disposable needle hair transplanter, which is disposable after used to avoid the risk of virus affection.

To achieve the above and other objects, the disposable needle hair transplanter of the present invention includes: a plunger structure having an outer barrel defining a passage, the passage having a first end and a second end, the plunger structure further having a reciprocally movable plunger assembly, the plunger assembly having at least one push needle up and down movable within the passage of the outer barrel, the plunger structure further having a hair transplantation depth controller drivingly connected with the plunger assembly via a link; a needle having a needle seat connected with a bottom section of the outer barrel and at least one needle tube connected with one end of the needle seat, whereby when the needle tube is thrust into the scalp, the hair transplantation depth controller restricts the depth by which the needle tube is thrust into the scalp; and a hair follicle depth controller having a cylindrical structure fitted around the needle seat and a shaft tube connected with a bottom section of the cylindrical structure and coaxially disposed around the needle tube, the needle tube extending out of the shaft tube by a predetermined length, whereby the hair transplantation depth controller is movably disposed around the shaft tube and movable along the shaft tube toward the scalp or away from the scalp.

The above disposable needle hair transplanter further includes a hair follicle loading tool for loading the hair follicle into the needle tube. The hair follicle loading tool includes a hair follicle fork having an outer diameter smaller than inner diameter of the needle tube. The front end of the hair follicle fork has a forked needle.

The present invention can be best understood through the following description and accompanying drawings, wherein:

DETAILED DESCRIPTION OF THE PREFERRED EMBODIMENTS

Figure 1:
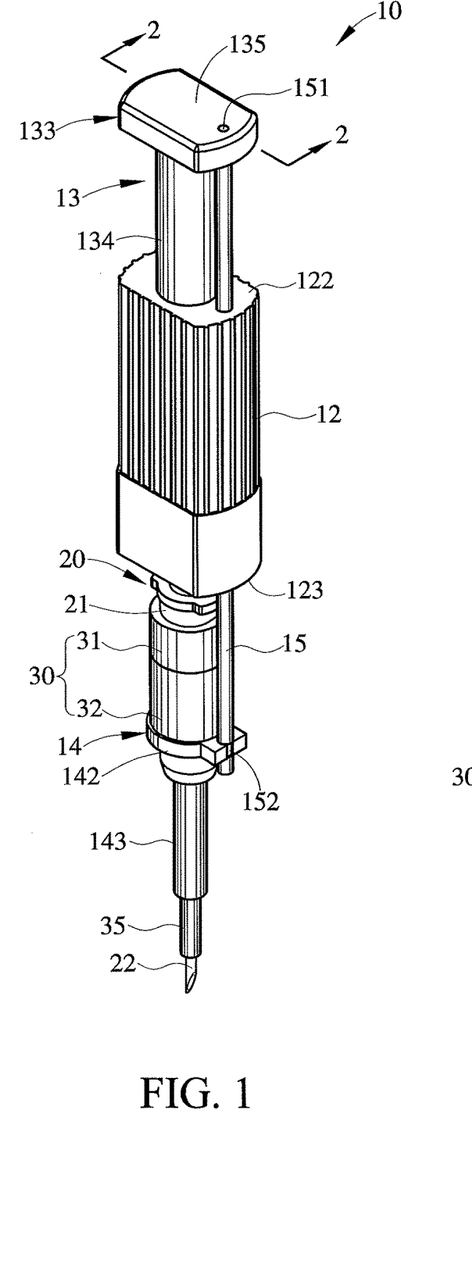
FIG. 1 is a perspective view of the present invention, showing a mono-needle structure.
Figure 2:
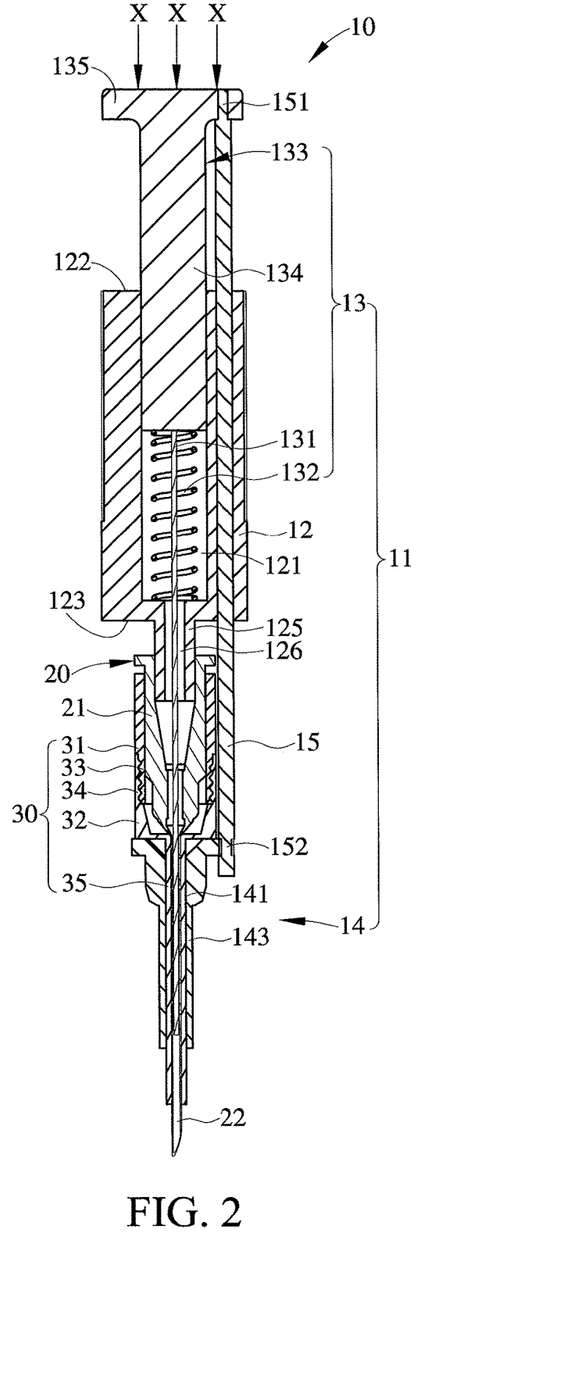
FIG. 2 is a sectional view taken along line 2-2 of FIG. 1.
Figure 3:
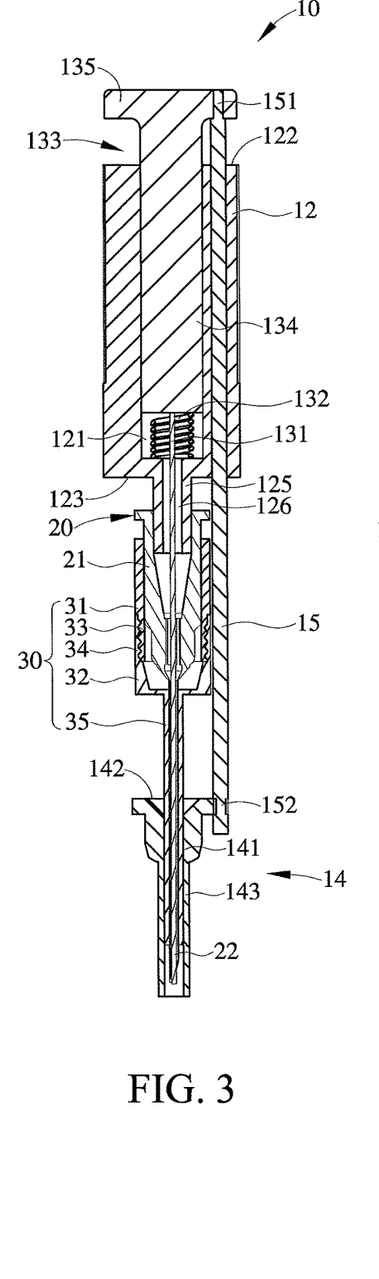
FIG. 3 is a sectional view according to FIG. 2, showing that a pressing force is applied to the plunger assembly of the present invention.

The disposable needle hair transplanters of the present invention can be classified into mono-needle type and multi-needle type. FIGS. 1 to 8C show a mono-needle type for illustration purposes. Please refer to FIGS. 1 and 2. The disposable needle hair transplanter 10 of the present invention includes a plunger structure 11, a needle 20 and a hair follicle depth controller 30. When a force is applied to the plunger structure 11 in X direction, the plunger structure 11 is moved between the positions as shown in FIGS. 2 and 3.

Figure 4:
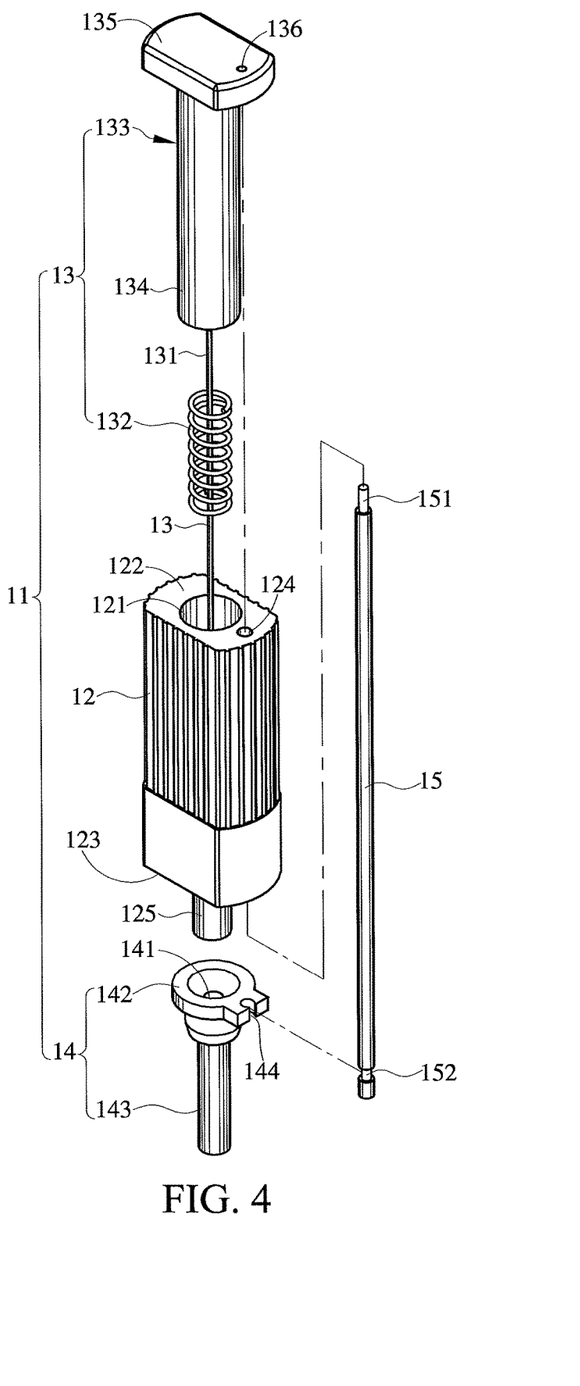
FIG. 4 is a perspective exploded view of the plunger structure of the present invention.

As shown in FIG. 4, the plunger structure 11 includes an outer barrel 12, a reciprocally movable plunger assembly 13 and a hair transplantation depth controller 14 drivingly connected with the plunger assembly 13 via a link 15. The outer barrel 12 defines a passage 121 having a first end 122 and a second end 123. The outer barrel 12 further includes a through hole 124 extending from the first end 122 to the second end 123, and a hub section 125 downward extending from the second end 123. The hub section 125 defines an internal hole 126 in communication with the passage 121. The internal hole 126 has a diameter smaller than that of the passage 121. Preferably, the link 15 can pass through the through hole 124 of the outer barrel 12. The link 15 has an upper end connection section 151 and a lower end connection section 152.

The plunger assembly 13 includes a push needle 131 vertically up and down movable within the passage 121 of the outer barrel 12. The push needle 131 extends from the passage 121 of the outer barrel 12 through the internal hole 126 of the hub section 125 and protrudes from the hub section 125 by a predetermined length. A spring 132 is disposed in the passage 121 of the outer barrel 12 and coaxially positioned around the push needle 131 for urging the push needle 131 to vertically up and down move within the passage 121 of the outer barrel 12. The plunger assembly 13 further includes a press member 133 having a plunger section 134 fixedly connected with the top end of the push needle 131 and vertically up and down movable within the passage 121 of the outer barrel 12. The press member 133 further includes a press section 135 formed at the top end of the plunger section 134 for an operator to apply a pressing force. The press section 135 has an insertion hole 136. The upper end connection section 151 of the link 15 is inserted in the insertion hole 136 to securely connect the link 15 with the press section 135. When a force is applied to the press member 133 in X direction (as shown in FIG. 2), the push needle 131 is moved forward and the plunger section 134 is moved to a position near the bottom end face of the passage 121 to compress the spring 132 into a compressed state (as shown in FIG. 3). When the press member 133 is released from the pressing force, the spring 132 elastically forces the plunger assembly 13 to restore to its home position.

The hair transplantation depth controller 14 is positioned under the outer barrel 12 without connecting with the outer barrel 12. The hair transplantation depth controller 14 defines an insertion passage 141 and has a connection end section 142 and a tubular end section 143 integrally connected with the connection end section 142. A lateral side of the connection end section 142 is formed with an engagement notch 144 for securely engaging with the lower end connection section 152 of the link 15. Accordingly, via the link 15, the plunger assembly 13 can force the hair transplantation depth controller 14 to move forward or backward in an axial direction.

Figure 5:
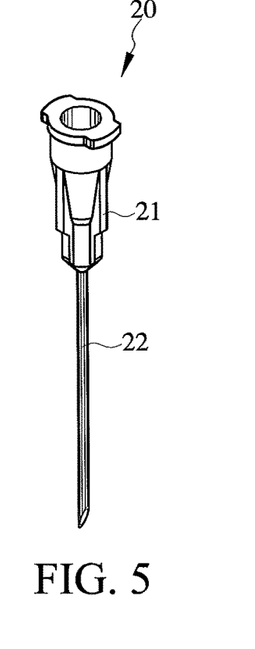
FIG. 5 is a perspective view of the needle of the present invention.

As shown in FIG. 5, the needle 20 has a needle seat 21 disposed around the hub section 125 to tightly connect the needle 20 with the outer barrel 12, and a needle tube 22 connected with one end of the needle seat 21. When the needle tube 22 is thrust into the scalp, the hair transplantation depth controller 14 restricts the depth by which the needle tube 22 is thrust into the scalp.

Figure 6:
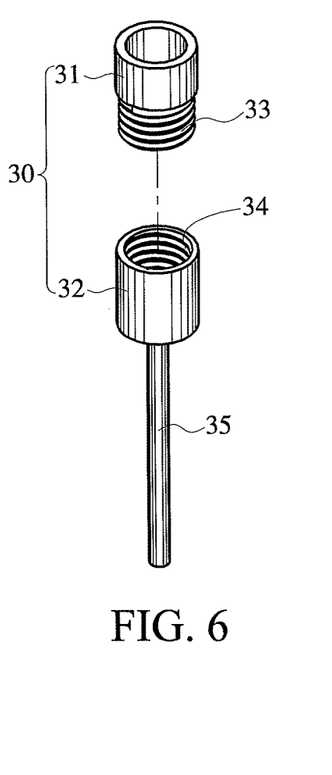
FIG. 6 is a perspective exploded view of the hair follicle depth controller of the present invention.
Figure 7:
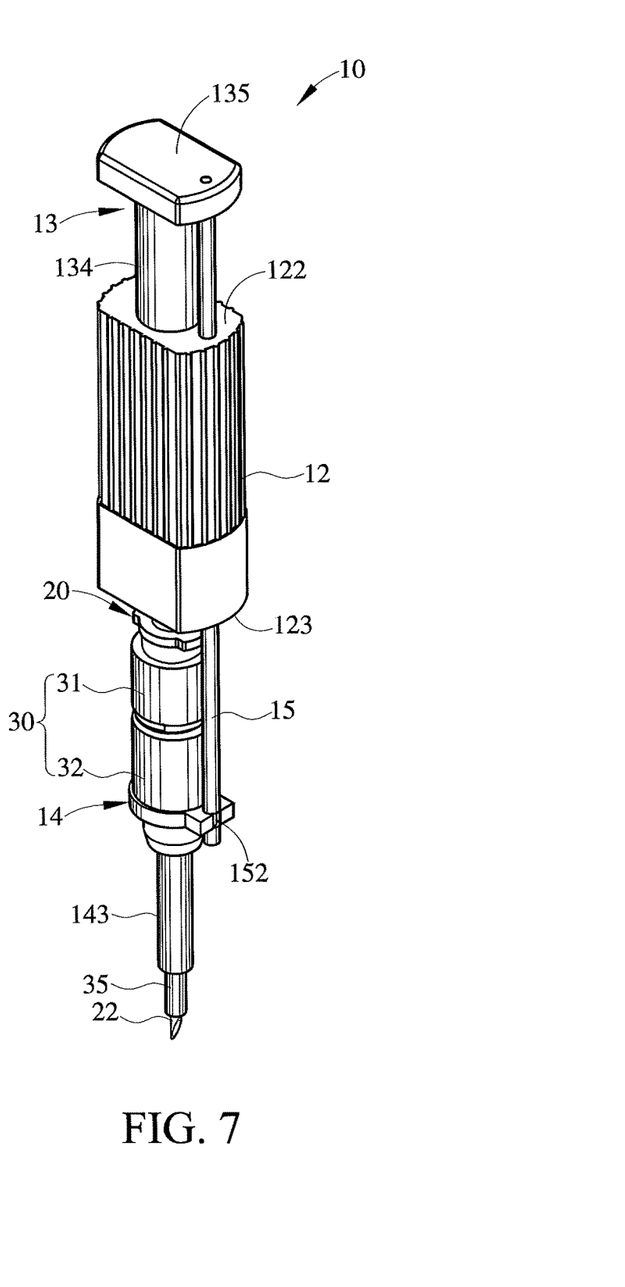
FIG. 7 is a perspective view showing that the upper and lower sleeves of the hair follicle depth controller of the present invention are unscrewed to extend the hair follicle depth controller.

As shown in FIG. 6, the hair follicle depth controller 30 has an upper sleeve 31 fitted around the needle seat 21 and a lower sleeve 32 connected with the upper sleeve 31 by means of threaded structures 33, 34 to form a cylindrical structure. By means of screwing/unscrewing the threaded structures 33, 34, the length of the hair follicle depth controller 30 can be adjusted so as to control the depth by which the hair follicle is transplanted into the scalp. Accordingly, by means of rotating the lower sleeve 32, the length of the hair follicle depth controller 30 can be elongated (as shown in FIG. 7) or shortened (as shown in FIG. 1). In practice, the end section of the lower sleeve 32 is formed with a shaft tube 35 coaxially disposed around the needle tube 22. The needle tube 22 extends out of the shaft tube 35 by a predetermined length. The shaft tube 35 is disposed in the insertion passage 141 of the hair transplantation depth controller 14, whereby the hair transplantation depth controller 14 is movably disposed around the shaft tube 35. In other words, the hair transplantation depth controller 14 can be moved along the shaft tube 35 toward the scalp or away from the scalp.

Figure 8:
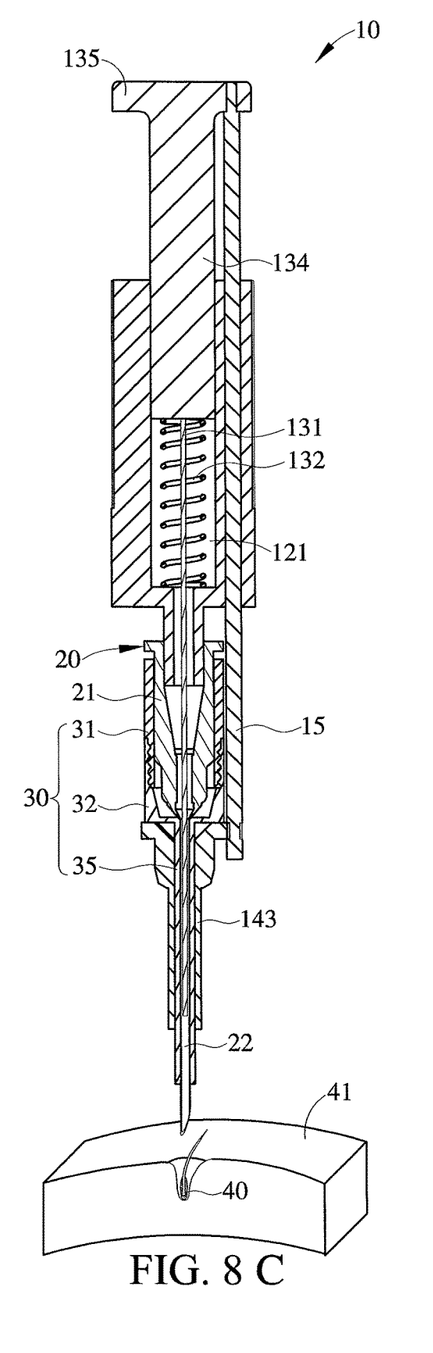
FIGS. 8A to 8C are sectional views showing that the disposable needle hair transplanter of the present invention is operated to transplant the hair follicle into the scalp.
Figure 8A:
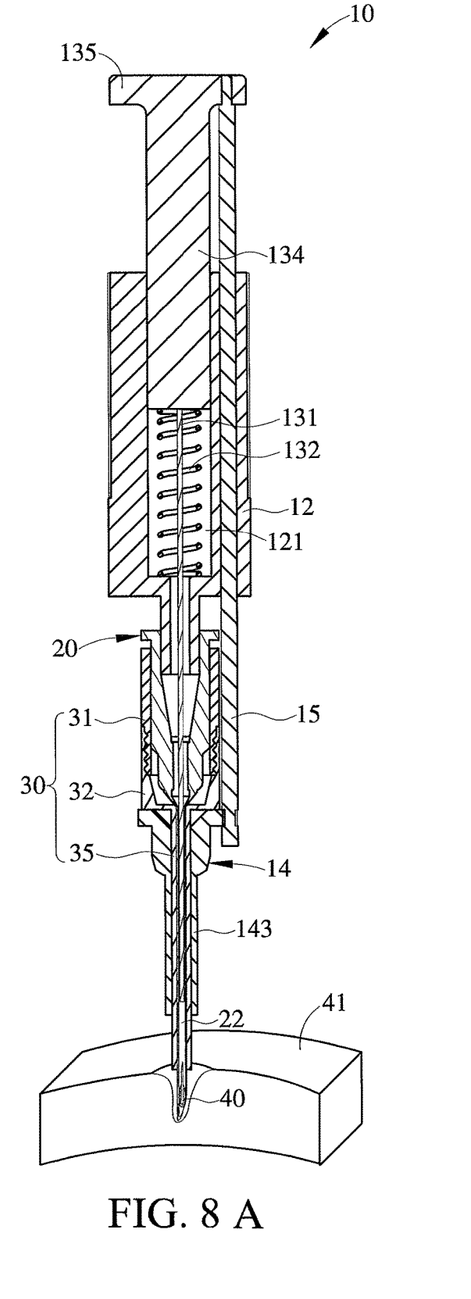
Figure 8B:
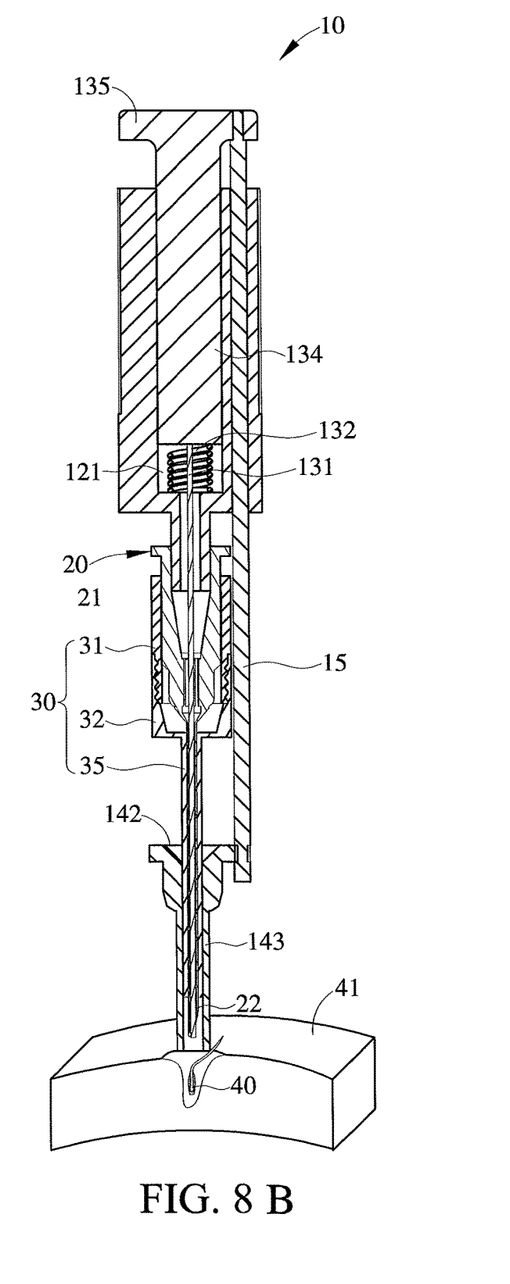

FIGS. 8A to 8C show that the disposable needle hair transplanter 10 of the present invention is operated to transplant the hair follicle 40 into the scalp 41. First, the hair follicle 40 is placed into the needle tube 22. Then, the needle tube 22 is thrust into the scalp 41 to fissure the scalp 41 until the shaft tube 35 of the hair follicle depth controller 30 contacts the surface of the scalp 41 as shown in FIG. 8A. Then, a downward force is applied to the press section 135 to move the push needle 131 downward. The tubular end section 143 of the hair transplantation depth controller 14 is driven by the link 15 to move downward into abutment against the surface of the scalp 41, whereby the shaft tube 35 and the needle tube 22 are forcedly retracted into the tubular end section 143 to extract the needle tube 22 from the scalp 41. At this time, the hair follicle 40 is fully transplanted into the scalp 41 and the spring 132 is in a compressed state as shown in FIG. 8B. Finally, the disposable needle hair transplanter 10 is removed and the press section 135 is released from the pressing force, whereby the spring 132 elastically extends to push the press member 133 upward to its home position as shown in FIG. 8C.

Figure 9:
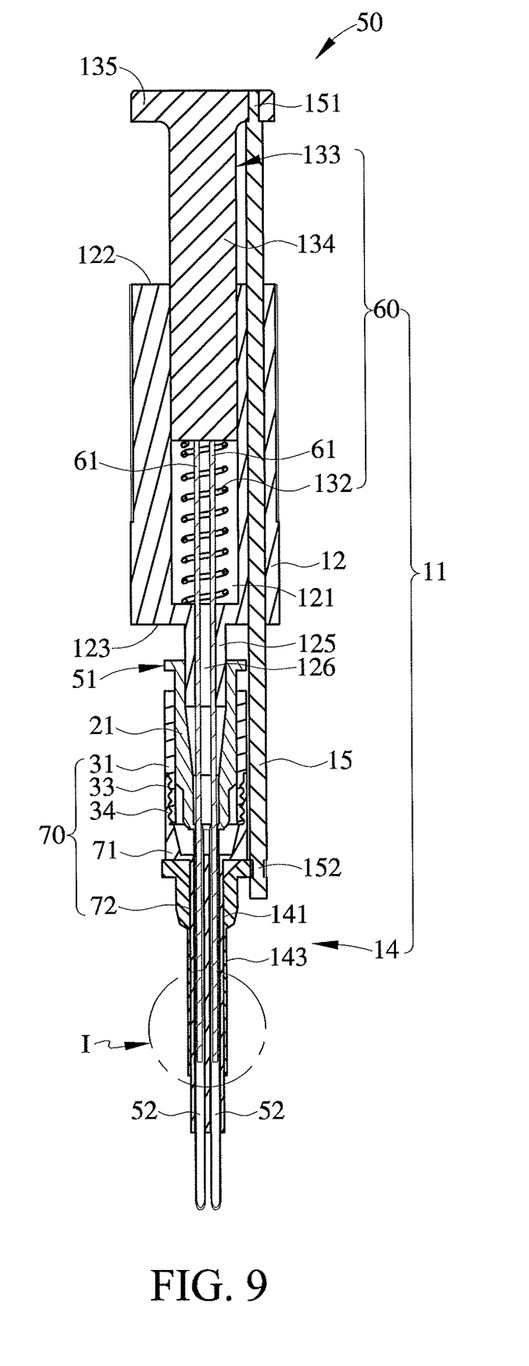
FIG. 9 is a sectional view of the disposable needle hair transplanter of the present invention, showing a multi-needle structure.
Figure 10:
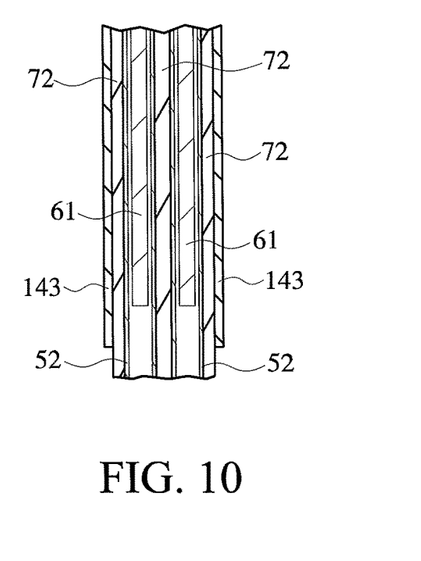
FIG. 10 is an enlarged view of circled area I of FIG. 9.

The disposable needle hair transplanter of the present invention is also applicable to multi-needle disposable needle hair transplanter. Please refer to FIGS. 9 and 10, which show a dual-needle disposable needle hair transplanter for illustration. The same components as those of FIGS. 1 to 8C are denoted with the same reference numerals. The components of the disposable needle hair transplanter 50 are identical to those of the embodiment of FIGS. 1 to 8C. However, in order to apply the disposable needle hair transplanter of the present invention to dual-needle disposable needle hair transplanter, the needle 51 has two needle tubes 52 and the plunger assembly 60 has two push needles 61 respectively extending through the needle tubes 52. The lower sleeve 71 of the hair follicle depth controller 70 is formed with a double-hole shaft tube 72 for receiving the needle tubes 52. The dual-needle disposable needle hair transplanter 50 can be operated to transplant two hair follicles into the scalp at the same time so as to save the time of hair transplantation and transplant the hairs more densely.

Figure 11:
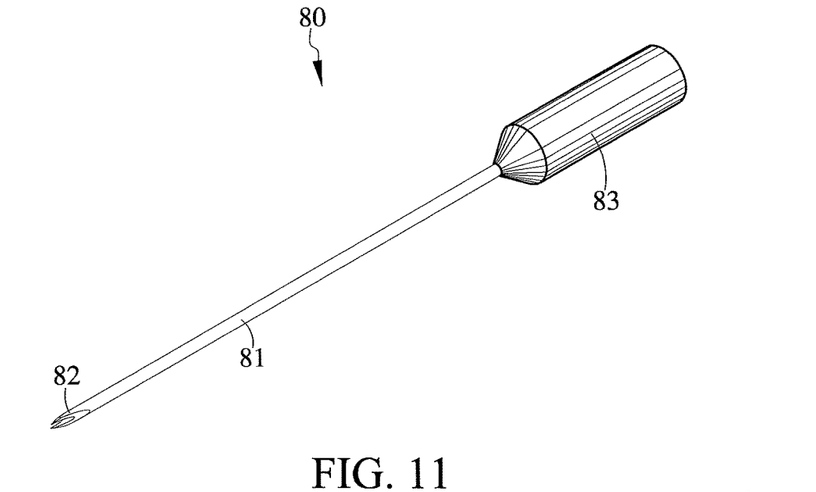
FIG. 11 is a perspective view of the hair follicle loading device of the present invention.
Figure 12:
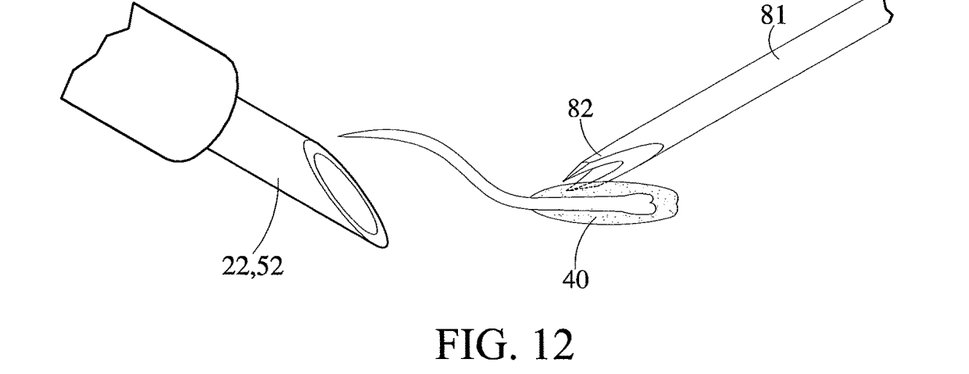
FIG. 12 is a perspective view according to FIG. 11, showing that the hair follicle loading device is used to load the hair follicle into the needle tube.

Please now refer to FIGS. 11 and 12. The disposable needle hair transplanter of the present invention further includes a hair follicle loading tool 80 for loading the hair follicle 40 into the needle tubes 22, 52. The hair follicle loading tool 80 includes a hair follicle fork 81 having an outer diameter smaller than inner diameter of the needle tubes 22, 52. The front end of the hair follicle fork 81 has a forked needle 82 in the form of a straight tube. By means of the forked needle 82, the hair follicle 40 can be quickly loaded into the needle tubes 22, 52. The hair follicle loading tool 80 further includes a handle section 83 connected with rear end of the hair follicle fork 81 for an operator to hold. When using the hair follicle loading tool 80 to load the hair follicle 40 into the needle tubes 22, 52, the forked needle 82 is first inserted into front end of the hair follicle 40. The forked needle 82 provides two force application points for loading the hair follicle 40 and ensures that the hair follicle 40 will not be penetrated. Also, the loading efficiency of the hair follicle 40 can be greatly enhanced.

Figure 13:
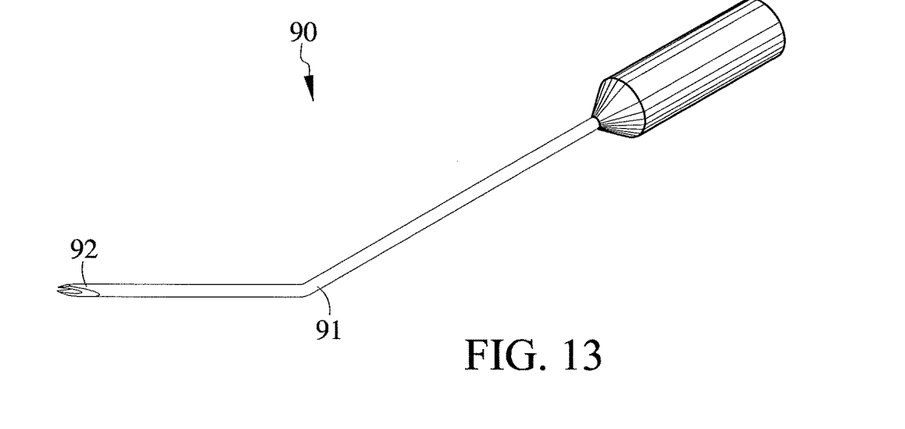
FIG. 13 is a perspective view of a second embodiment of the hair follicle loading device of the present invention.

FIG. 13 shows a second embodiment of the hair follicle loading tool. The components of the hair follicle loading tool 90 are identical to those of FIGS. 11 and 12. The hair follicle loading tool 90 has a hair follicle fork 91 and a forked needle 92 formed at the front end of the hair follicle fork 91. The second embodiment is different from the first embodiment in that the hair follicle fork 91 is bent to facilitate the loading of the hair follicle into the needle tube.

The above embodiments are only used to illustrate the present invention, not intended to limit the scope thereof. Many modifications of the above embodiments can be made without departing from the spirit of the present invention.

What is claimed is:

1. A disposable needle hair transplanter for transplanting hair follicles into a scalp, the disposable needle hair transplanter comprising:
    a plunger structure having an outer barrel defining a passage, the passage having a first end and a second end, the plunger structure further having a reciprocally movable plunger assembly, the plunger assembly having at least one push needle up and down movable within the passage of the outer barrel, the plunger structure further having a hair transplantation depth controller drivingly connected with the plunger assembly via a link;
    a needle having a needle seat connected with a bottom section of the outer barrel and at least one needle tube connected with one end of the needle seat, whereby when the needle tube is thrust into the scalp, the hair transplantation depth controller restricts the depth by which the needle tube is thrust into the scalp; and
    a hair follicle depth controller having a cylindrical structure fitted around the needle seat and a shaft tube connected with a bottom section of the cylindrical structure and coaxially disposed around the needle tube, the needle tube extending out of the shaft tube by a predetermined length, whereby the hair transplantation depth controller is movably disposed around the shaft tube and movable along the shaft tube toward the scalp or away from the scalp.

2. The disposable needle hair transplanter as claimed in claim 1, wherein the outer barrel further includes a through hole extending from the first end to the second end, the link passing through the through hole to drivingly connect with the plunger assembly and the hair transplantation depth controller, the outer barrel further including a hub section downward extending from the second end, the hub section defining an internal hole in communication with the passage.

3. The disposable needle hair transplanter as claimed in claim 2, wherein the link has an upper end connection section connected with the plunger assembly and a lower end connection section connected with the hair transplantation depth controller.

4. The disposable needle hair transplanter as claimed in claim 1, wherein the plunger assembly further includes a press member fixedly connected with a top end of the push needle for pushing the push needle to move downward.

5. The disposable needle hair transplanter as claimed in claim 4, wherein via a spring, the press member urges the push needle to move toward the scalp or away from the scalp.

6. The disposable needle hair transplanter as claimed in claim 1, wherein the hair transplantation depth controller has a connection end section and a tubular end section integrally connected with the connection end section, a lateral side of the connection end section being formed with an engagement notch for securely engaging with one end of the link.

7. The disposable needle hair transplanter as claimed in claim 1, wherein the cylindrical structure of the hair follicle depth controller is composed of an upper sleeve and a lower sleeve connected with the shaft tube, the upper and lower sleeves being connected with each other by means of threaded structures, by means of screwing/unscrewing the threaded structures, the length of the hair follicle depth controller being adjustable.

8. The disposable needle hair transplanter as claimed in claim 1, wherein the shaft tube of the hair follicle depth controller is formed with at least one hole for receiving at least one needle tube.

9. The disposable needle hair transplanter as claimed in claim 1, further comprising a hair follicle loading tool for loading the hair follicle into the needle tube, the hair follicle loading tool including a hair follicle fork having an outer diameter smaller than inner diameter of the needle tube.

10. The disposable needle hair transplanter as claimed in claim 9, wherein a front end of the hair follicle fork has a forked needle.

11. The disposable needle hair transplanter as claimed in claim 9, wherein the hair follicle fork is bent.

* * * * *